United States Patent [19]

Kuhla et al.

[11] 3,961,067

[45] June 1, 1976

[54] COMPOSITION COMPRISING A BENZENESULFONYLUREA HYPOGLYCEMIC AGENT AND METHOD OF TREATMENT

[75] Inventors: Donald E. Kuhla, Gales Ferry; Reinhard Sarges, Mystic; Hans E. Wiedermann, Niantic, all of Conn.

[73] Assignee: Pfizer Inc., New York, N.Y.

[22] Filed: Oct. 21, 1974

[21] Appl. No.: 516,372

Related U.S. Application Data

[62] Division of Ser. No. 338,965, March 7, 1973, Pat. No. 3,856,806.

[52] U.S. Cl. ................................. 424/270
[51] Int. Cl.² ........................... A61K 31/425
[58] Field of Search ........................ 424/270

[56] References Cited
UNITED STATES PATENTS 3,755,587  8/1973  Plumpe et al. ............ 424/270 X

FOREIGN PATENTS OR APPLICATIONS 1,244,593  9/1971  United Kingdom ............ 424/270

*Primary Examiner*—Frederick E. Waddell
*Attorney, Agent, or Firm*—Connolly and Hutz

[57] ABSTRACT

Several benzenesulfonylurea compounds derived from 4-methyl-5-thiazolecarboxylic acid have been prepared by reacting 4-[2-(4-methyl-5-thiazolecarboxamido)ethyl]benzenesulfonamide with an appropriate organic isocyanate or a trisubstituted urea equivalent thereof. The sulfonylureas so obtained are useful in therapy as oral hypoglycemic agents. 1-Cyclohexyl-3-{4-[2-(4-methyl-5-thiazolecarboxamido)ethyl]benzenesulfonyl} urea represents a preferred embodiment.

7 Claims, No Drawings

COMPOSITION COMPRISING A BENZENESULFONYLUREA HYPOGLYCEMIC AGENT AND METHOD OF TREATMENT

This application is a divisional of application Ser. No. 338,965 filed Mar. 7, 1973 and now U.S. Pat. No. 3,856,806.

BACKGROUND OF THE INVENTION

This invention relates to new and useful sulfonylurea derivatives, which are effective in reducing blood sugar levels to a remarkably high degree. More particularly, it is concerned with certain benzenesulfonylureas and their base salts with pharmacologically acceptable cations, which are useful in therapy as oral hypoglycemic agents for the treatment of diabetes.

In the past, various attempts have been made by numerous investigators in the field of organic medicinal chemistry to obtain new and better oral hypoglycemic agents. For the most part, these efforts have principally involved the synthesis and testing of various new and heretofore unavailable organic compounds, particularly in the area of the sulfonylureas and the various biguanidine derivatives. However, in the search for still newer and more improved oral hypoglycemic agents, far less is known about the activity of various substituted carboxamidobenzenesulfonylureas such as those which are derived from certain heterocyclic monocarboxylic acids. For instance, French Pat. No. 8220M discloses several acylamino-derived benzenesulfonylureas which contain an isothiazole ring and are reported to be active as hypoglycemic agents, but none of these aforementioned compounds presently possess any known clinical advantages over either chlorpropamide or tolbutamide when used in the treatment of diabetes.

SUMMARY OF THE INVENTION

In accordance with the present invention, it has now been rather surprisingly found that certain novel benzenesulfonylureas derived from 4-methyl-5-thiazolecarboxylic acid are extremely useful when employed as oral hypoglycemic agents for the multiple daily dosing of diabetic subjects. The novel sulfonylurea compounds of this invention are all selected from the group consisting of benzenesulfonylureas of the formula:

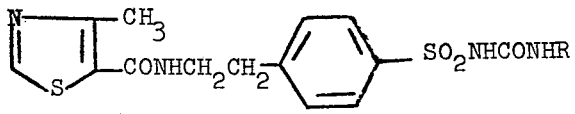

and the base salts thereof with pharmacologically acceptable cations, wherein R is bicyclo [2.2.1]hept-5-en-2-yl-endo-methyl or cycloalkyl having from five to seven carbon atoms. Typical member compounds specifically embraced by this invention include 1-(bicyclo[2.2.1]hept-5-en-2-yl-endo-methyl)-3-{4-[2-(4-methyl-5-thiazolecarboxamido)ethyl]benzenesulfonyl}urea, 1-cyclopentyl-3-{4-[2-(4-methyl-5-thiazolecarboxamido)ethyl]benzenesulfonyl}urea, 1-cyclohexyl-3-{4-[2-(4-methyl-5-thiazolecarboxamido)ethyl]benzenesulfonyl}urea and 1-cycloheptyl-3- 4-[2-(4-methyl-5-thiazolecarboxamido)ethyl]benzenesulfonyl urea, and their corresponding sodium salts. These particular compounds are all highly potent as regards their hypoglycemic activity and therefore are extremely useful in lowering blood sugar levels when given by the oral route of administration. Moreover, these novel agents all possess an ultra-short half-life and hence, give smoother control of blood glucose levels when used several times per day in divided doses for the present purposes at hand.

DETAILED DESCRIPTION OF THE INVENTION

In accordance with the process employed for preparing the novel compounds of this invention, 4-[2-(4-methyl-5-thiazolecarboxamido)ethyl]benzenesulfonamide is reacted with an organic isocyanate reagent of the formula RNCO wherein R corresponds to the previously defined 1-substituent on the urea moiety of the desired final product. In this way, the corresponding 4-[2-(4-methyl-5-thiazolecarboxamido)ethyl]benzenesulfonylurea compound is formed having the requisite structural formula previously indicated. This particular reaction is normally conducted in a basic solvent medium, most desirably employing an aprotic organic solvent such as tetrahydrofuran, dimethylsulfoxide or dimethylformamide and preferably using a slight excess in moles of a base, like triethylamine or sodium hydride (in mineral oil), which may then be admixed with the solvent. Many of the aforesaid isocyanate reagents (RNCO) are either known compounds or else they can easily be prepared, using methods well-known to those skilled in the art, starting from readily available materials. In practice, it is usually preferable to employ at least about a molar equivalent of the isocyanate reagent in the aforesaid reaction of the present invention, with best results often being achieved by using a slight excess of same. Although any temperature below that of reflux may be used in order to effect the reaction, it is normally found most convenient in practice to employ elevated temperatures so as to shorten the required reaction time, which may range anywhere from several minutes up to about 24 hours depending, of course, upon the particular benzenesulfonylurea actually being prepared. Upon completion of the reaction, the product is easily recovered from the spent reaction mixture in a conventional manner, e.g., by pouring the mixture into an excess of ice-water containing a slight excess of acid, such as hydrochloric acid, whereby the desired benzenesulfonylurea readily precipitates from solution and is subsequently collected by such means as suction filtration and the like.

Another method for preparing the novel compounds of this invention involves reacting 4-[2-(4-methyl-5-thiazolecarboxamido)-ethyl]benzenesulfonamide in the form of an alkali metal or alkaline-earth metal salt (either employed as such or else formed in situ) with an appropriate 1,1,3-trisubstituted urea of the formula (R')$_2$NCONHR, wherein R' is an aryl group such as phenyl, p-chlorophenyl, p-bromophenyl, p-nitrophenyl, p-acetylaminophenyl, p-tolyl, p-anisyl, α-naphthyl, β-naphthyl and the like. This reaction is preferably carried out in the presence of an inert polar organic solvent medium. Typical organic solvents for use in this connection include the N,N-dialkyl lower alkanoamides like dimethylformamide, dimethylacetamide, diethylformamide and diethylacetamide, as well as lower dialkyl sulfoxides such as dimethyl sulfoxide, diethyl sulfoxide and di-n-propyl sulfoxide, etc. It is desirable that the aforesaid solvent for this reaction be present in sufficient amount to dissolve each of the previously mentioned starting materials. In general, the reaction is conducted at a temperature that is in the range of from about 20°C. up to about 150°C. for a period of about ½ to about 10 hours. The relative amounts of reagents employed are such that the molar ratio of said benzenesulfonamide to the 1,1-diaryl-3-(monosubstituted)urea is most desirably in the range of from about 1:1 to about 1:2, respectively. Recovery of the desired product from the reaction mixture is then achieved by first diluting the reaction solution with water and thereafter adjusting if necessary the pH of the resulting solution to a value of at least about 8.0, followed by thorough extraction of the basis aqueous solution with any water-immiscible organic solvent in order to remove the diarylamine byproduct of formula $(R')_2NH$ as well as minor amounts of unreacted or excess starting material that might still possibly be present. Isolation of the desired benzenesulfonylurea from the basic aqueous layer is then finally accomplished by adding a sufficient amount of a dilute aqouesu acid to the aforesaid basic solution to cause precipitation of the desired sulfonylurea therefrom.

The major starting materials required for this reaction, viz., 4-[2-(4-methyl-5-thiazolecarboxamido)ethyl]benzenesulfonamide and the 1,1-diaryl-3-(monosubstituted)ureas, are readily prepared by those skilled in the art in accordance with the conventional methods of organic chemistry. For instance, 4-[2-(4-methyl-5-thiazolecarboxamido)ethyl]benzenesulfonamide, which is also the same compound used as starting material in the previously described isocyanate method, is suitably obtained by using classical methods of organic synthesis starting from the known 4-(2-aminoethyl)benzenesulfonamide and proceeding in accordance with the procedure described in the experimental section of this specification in some detail (e.g., see Preparation A in this regard). The 1,1-diaryl-3-(monosubstituted)ureas, on the other hand, are all readily prepared from common organic reagents by employing standard procedures well known in the art. For example, the desired 1,1,3-trisubstituted urea may simply be obtained by treating the corresponding disubstituted carbamyl chloride $[(R')_2NCOCl]$ with the appropriate amine $(RNH_2)$ in accordance with the general reaction procedure described by J.F.L. Reudler in *Recueil des Travaux Chimiques des Pays-Bas.*, Vol. 33, p. 64 (1914).

The chemical bases which are used as reagents in this invention to prepare the aforementioned pharmaceutically acceptable base salts are those which form non-toxic salts with the herein described acidic benzenesulfonylureas, such as 1-cyclohexyl-3-{4[-[2-(4-methyl-5-thiazolecarboxamido)ethyl]benzenesulfonyl}urea, for example. These particular non-toxic base salts are of such a nature that their cations are deemed to be essentially non-toxic in character over the wide range of dosage administered. Examples of such cations include those of sodium, potassium, calcium and magnesium, etc. These salts can easily be prepared by simply treating the aforementioned benzenesulfonylureas with an aqueous solution of the desired pharmacologically acceptable base, i.e., those oxides, hydroxides, or carbonates which contain pharmacologically acceptable cations, and then evaporating the resulting solution to dryness while preferably being placed under reduced pressure. Alternatively, they may also be prepared by mixing lower alkanolic solutions of the said acidic compounds and the desired alkali metal alkoxide together, and then evaporating the resulting aforesaid solution in the same manner as before. In either case, stoichiometric amounts of reagents must be employed in order to ensure completeness of reaction and consequent maximum production of yields with respect to the desired salt product.

As previously indicated, the benzenesulfonylurea compounds of this invention are all readily adapted to therapeutic use as oral hypoglycemic agents, in view of their ability to lower the blood sugar levels of diabetic and non-diabetic subjects to a statistically significant degree. For instance, 1-cyclohexyl-3-{4-[2-(4-methyl-5-thiazolecarboxamido)ethyl]benzenesulfonyl}urea (as the sodium salt), a typical and preferred agent of the present invention, has been found to consistently lower blood sugar levels in the normal fasted rat to a statistically significant degree when given by either the oral or the intraperitoneal route of administration at dose levels ranging in either case from 0.5 mg./kg. to 5.0 mg./kg., respectively, without showing any substantial signs of toxic side effects. The other compounds of this invention also cause similar results. Furthermore, all the herein described compounds of this invention can be administered for the present purposes at hand without causing any significant untoward pharmacological side reactions to occur in the subject to whom they are so administered. In general, these compounds are ordinarily administered at dosage levels ranging from about 0.05 mg. to about 1.0 mg. per kg. of body weight per day, although variations will necessarily occur depending upon the condition and individual response of the subject being treated and the particular type of oral formulation chosen.

In connection with the use of the benzenesulfonylurea compounds of this invention for the treatment of diabetic subjects, it is to be noted that they may be administered either alone or in combination with pharmaceutically acceptable carriers and that such administration can be carried out in both single and multiple dosages. More particularly, the novel compounds of the invention can be administered in a wide variety of different dosage forms, i.e., they may be combined with various pharmaceutically-acceptable inert carriers in the form of tablets, capsules, lozenges, troches, hard candies, powders, aqueous suspensions, elixirs, syrups and the like. Such carriers include solid diluents or fillers, sterile aqueous media and various non-toxic organic solvents, etc. Moreover, such oral pharmaceutical compositions can be suitably sweetened and/or flavored by means of various agents of the type commonly employed for just such a purpose. In general, the therapeutically-effective compounds of this invention are present in such dosage forms at concentration levels ranging from about 0.5 to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and- /or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as hypoglycemic agents, is determined by their ability to lower blood sugar levels in the normal fasted rat when tested therein for such purposes according to the procedure described by W. S. Hoffman, as reported in the *Journal of Biological Chemistry*, Vol. 120, p. 51 (1937). The latter method measures directly the amount of glucose in the blood at any given time and from this, the maximum percent decrease in blood sugar can be readily calculated and reported as hypoglycemic activity per se. In this way, the present benzenesulfonylurea compounds are shown to markedly reduce the blood sugar levels of non-anesthetized rats when administered to them at dose levels as low as 0.5 mg./kg.

PREPARATION A

To a suspension of 0.715 g. (0.005 mole) of 4-methyl-5-thiazolecarboxylic acid [prepared according to the procedure of J. D'Amico et al., *Journal of Organic Chemistry*, Vol. 25, p. 1336 (1960)] in 7.0 ml. of carbon tetrachloride, there were added 7.0 ml. of thionyl chloride which had also been dissolved in 7.0 ml. of carbon tetrachloride. The resulting mixture was then refluxed on a steam bath for a period of 1 hour, at which point no further evolution of hydrogen chloride and sulfur dioxide gas could be detected. The homogeneous reaction mixture so obtained was then refluxed for an additional period of 10 minutes, cooled to ambient temperatures and ultimately evaporated to near dryness while under reduced pressure to yield a residue substantially free of solvent and excess thionyl chloride. The latter material (i.e., the crude product) was thereafter dissolved in 20 ml. of benzene and again evaporated to near dryness while under reduced pressure. This particular purification step was repeated twice in order to remove the last traces of residual hydrogen chloride and thionyl chloride from the desired product. In this way, there was eventually obtained a quantitative yield of substantially pure 4-methyl-5-thiazolecarboxylic acid chloride, which was used in the next reaction step without any further purification being necessary.

To a mixture of 1.18 g. (0.005 mole) of 4-(2-aminoethyl)-benzenesulfonamide hydrochloride [E. Miller et al., *Journal of the American Chemical Society*, Vol. 62, p. 2099 (1940)] and 1.4 ml. (0.010 mole) of triethylamine in 15 ml. of dry tetrahydrofuran, there was added 805 mg. (0.005 mole) of 4-methyl-5-thiazolecarboxylic acid chloride dissolved in 15 ml. of tetrahydrofuran. The addition caused a slight exothermic reaction to occur, after which the reaction mixture was allowed to stand at ambient temperatures for a period of approximately 16 hours with constant agitation being maintained throughout the entire step. At this point, the spent mixture was poured into 50 ml. of ice water and subsequently acidified with a few drops of 3N aqueous hydrochloric acid. The resulting cream-colored precipitate was then recovered by means of suction filtration, washed well with cold water and thereafter crystallized from acetonitrile (after treatment with activated carbon) to yield 1.8 g (73%) of pure 4-[2-methyl-5-thiazolecarboxamido)ethyl]benzenesulfonamide, m.p. 182°–183°C.

Anal. Calcd. for $C_{13}H_{15}N_3O_3S_2$: C, 47.98; H, 4.65; N, 12.91. Found: C, 48.13; H, 4.60; N, 12.91.

PREPARATION B

A 500 ml. three-necked, round-bottomed flask was charged with 14.6 g. (0.119 mole) of endo-2-aminomethylbicyclo[2.2.1]hept-5-ene [P. Wilder et al., *Journal of Organic Chemistry*, Vol. 30, p. 3078 (1965)], 18.0 g (0.178 mole) of triethylamine and 100 ml. of tetrahydrofuran. The mixture was then rapidly cooled and stirred in an ice bath, while a solution consisting of 27.4 g. (0.119 mole) of N,N-diphenylcarbamoyl chloride dissolved in 100 ml. of tetrahydrofuran was slowly added thereto in a dropwise manner. After the addition was complete, the reaction mixture was stirred at room temperature (~25°C.) for a period of 1 hour and the resulting solution was then concentrated in vacuo (to approximately one-third of its original volume) to remove most of the tetrahydrofuran. On cooling, there was obtained a crystalline precipitate, which was subsequently collected by means of suction filtration and thereafter suspended in 250 ml. of 1N aqueous hydrochloric acid. Extraction of the latter aqueous solution with three 200 ml. portions of chloroform, followed by drying of the combined organic extracts then gave a clear organic solution upon filtration. After evaporating the clear filtrate to near dryness while under reduced pressure, there was ultimately obtained a heavy viscous oil, which subsequently crystallized on trituration with n-hexane. Recrystallization of the latter solid material from diethyl ether/n-hexane then gave pure 1,1-diphenyl-3-(bicyclo[2.2.1]hept-5-en-2-yl-endo-methyl)-urea, m.p. 129°–130°C. The analytical sample was a crystalline white solid.

Anal. Calcd. for $C_{21}H_{22}N_2O$: C, 79.22; H, 6.96; N, 8.80. Found: C, 79.19; H, 7.05; N, 8.93.

EXAMPLE 1

To a well-stirred solution (cooled in an ice bath) consisting of 651 mg. (0.002 mole) of 4-[2-(4-methyl-5-thiazolecarboxamido)-ethyl]benzenesulfonamide dissolved in 5.0 ml. of dry N,N-dimethylformamide, there were added 500 mg. (0.004 mole) of cyclohexyl isocyanate, followed by 180 mg. (0.004 mole) of 56% sodium hydride in mineral oil. A white precipitate soon formed and vigorous hydrogen gas evolution was noted. The resulting mixture was then stirred at ambient temperatures for a period of approximately 2 hours, at which point thin-layer chromatography (TLC) analysis of an aliquot portion showed essentially complete conversion. After pouring the mixture into 50 ml. of anhydrous diethyl ether, the sodium salt of the product precipitated as a white solid and was subsequently collected by means of suction filtration. The filter cake was washed well with diethyl ether and then dissolved in 20 ml. of water. Upon acidification with 3N hydrochloric acid and extraction into chloroform, followed by decolorization with charcoal and drying over anhydrous magnesium sulfate, there was ultimately obtained a clear chloroform solution of the desired final product. Evaporation of the latter solution to near dryness while under reduced pressure then gave 704 mg. of pure 1-cyclohexyl-3-{4-[2-(4-methyl-5-thiazolecarboxamido)-ethyl]benzenesulfonyl}urea as a colorless oil, which subsequently crystallized from acetonitrile in the form of white needles melting at 199°–200°C. The yield of pure crystalline material amounted to 506 mg. (56%).

Anal. Calcd. for $C_{20}H_{26}N_4O_4S_2$: C, 53.31; H, 5.81; N, 12.43. Found: C, 53.53; H, 5.94; N, 12.13.

EXAMPLE II

The procedure described in Example I was repeated except that 1,1-diphenyl-3-(bicyclo[2.2.1]hept-5-en-2-yl-endo-methyl)urea was the reagent of choice employed in lieu of cyclohexyl isocyanate, on the same molar basis as before. In this particular case, the corresponding final product obtained was 1-(bicyclo[2.2.1]hept-5-en-2-yl-endo-methyl)-3-{4-[2-(4-methyl-5-thiazolecarboxamido)ethyl]benzenesulfonyl}urea, m.p. 153°–155°C.

Anal. Calcd. for $C_{22}H_{26}N_4O_4S_2$: C, 55.65; H, 5.52; N, 11.81. Found: C, 55.41; H, 5.54; N, 11.72.

EXAMPLE III

The procedure described in Example I is repeated except that cyclopentyl isocyanate is the reagent of choice employed in lieu of cyclohexyl isocyanate, on the same molar basis as before. In this particular case, the corresponding final porudct is 1-cyclopentyl-3-{4-[4-methyl-5-thiazolecarboxamido)ethyl]benzenesulfonyl}urea.

In like manner, the use of 1,1-diphenyl-3-cycloheptylurea in place of cyclohexyl isocyanate in the same reaction procedure described above affords 1-cycloheptyl-3-{4-[2-(4-methyl-5-thiazolecarboxamido)ethyl]benzenesulfonyl}urea as the desired final product.

EXAMPLE IV

The sodium salt of 1-cyclohexyl-3-{4-[2-(4-methyl-5-thiazolecarboxamido)ethyl]benzenesulfonyl}urea is prepared by dissolving said compound in anhydrous methanol and then adding said solution to another methanolic solution which contains an equivalent amount in moles of sodium methoxide. Upon subsequent evaporation of the solvent therefrom via freeze-drying, there is obtained the desired alkali metal salt in the form of an amorphous solid powder which is freely soluble in water.

In like manner, the potassium and lithium salts are also similarly prepared, as are the alkali metal salts of the other benzenesulfonylureas of this invention which are reported in the previous examples.

EXAMPLE V

The calcium slat of 1-(bicyclo[2.2.1]hept-5-en-2-yl-endo-methyl)-3-{4-[2-(4-methyl-5-thiazolecarboxamido)ethyl]benzenesulfonyl}urea is prepared by dissolving said compound in water containing an equivalent amount in moles of calcium hydroxide and then freeze-drying the mixture. The corresponding magnesium salt is also prepared in like manner, as are all the other alkaline-earth metal salts not only of this particular compound, but also of those acidic benzenesulfonylureas previously described in Examples I and III, respectively.

EXAMPLE VI

A dry solid pharmaceutical composition is prepared by blending the following materials together in the proportions by weight specified below:

| | |
|---|---|
| 1-Cyclohexyl-3-{4-[2-(4-methyl-5-thiazolecarboxamido)-ethyl]benzenesulfonyl}urea | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 50 mg. of the active ingredient. Other tablets are also prepared in a similar fashion containing 2.5, 5, 10, and 25 mg. of the active ingredient, respectively, by merely using the appropriate amount of the benzenesulfonylurea in each case.

EXAMPLE VII

A dry solid pharmaceutical composition is prepared by combining the following materials together in the proportions by weight indicated below:

| | |
|---|---|
| 1-(Bicyclo[2.2.1]hept-5-en-2-yl-endo-methyl)-3-{4-[2-(4-methyl-5-thiazolecarboxamido)ethyl]benzenesulfonyl}urea | .50 |
| Calcium carbonate | .20 |
| Polyethylene glycol, average molecular weight, 4000 | .30 |

The dried solid mixture so prepared is then thoroughly agitated so as to obtain a powdered product that is completely uniform in every respect. Soft elastic and hard-filled gelatin capsule containing this pharmaceutical composition are then prepared, employing a sufficient quantity of material in each instance so as to provide each capsule with 75 mg. of the active ingredient.

EXAMPLE VIII

The benzenesulfonylurea products of Examples I–II were tested for hypoglycemic activity in groups of six male albino rats (each weighing approximately 190–240 g.) of the Sprague-Dawley strain. No anesthetic was used in this study. The rats were fasted for approximately 18–24 hours prior to administration, a blood sample was then taken from the tail vein of each animal and the test compound was administered intraperitoneally (while in solution as the sodium salt in 0.9% saline) at dose levels of 5.0, 1.0 and 0.5 mg./kg., respectively. Additional blood samples were then taken at 1, 2 and 4 hour intervals after administration of the drug. The samples were immediately diluted 1:10 (by volume) with 1.0% heparin in 0.9% saline. Blood glucose was determined by adapting the method of W.S. Hoffman [see *Journal of Biological Chemistry*, Vol. 120, p. 51 (1937)] to the Autoanalyzer Instrument produced by Technicon Instruments Corporation of Chauncey, N.Y. On this basis, the maximum percent decrease in blood sugar was calculated and reported as such (i.e., as hypoglycemic activity) for the two compounds listed in the table below:

| Sulfonylurea | Hypoglycemic Activity (Max.%Fall) | | |
|---|---|---|---|
| | 0.5mg./kg. | 1.0mg/kg. | 5.0mg./kg. |
| Prod. of Ex. I | 17 | 41 | 43 |
| Prod. of Ex.II | 11 | 39 | 43 |

What is claimed is:

1. A method for lowering blood sugar in the treatment of a diabetic animal, which comprises orally administering to said animal an effective blood sugar lowering amount of a compound selected from the group consisting of a benzenesulfonylurea of the formula:

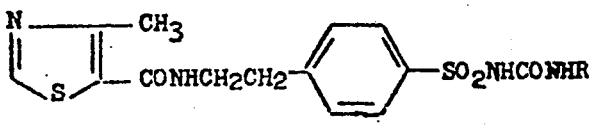

and a base salt thereof with a pharmacologically acceptable cation, wherein R is bicyclo [2.2.1]hept-5-en-2-yl-endo-methyl or cycloalkyl of from five to seven carbon atoms.

2. The method of claim 1 wherein the compound administered is 1-cyclohexyl-3-{4-[2-(4-methyl-5-thiazolecarboxamido)ethyl]benzenesulfonyl}urea.

3. The method of claim 1 wherein the compound administered is 1-(bicyclo[2.2.1]hept-5-en-2-yl-endo-methyl)-3-{4-[2-(4-methyl-5-thiazolecarboxamido)ethyl]benzenesulfonyl}urea.

4. A composition for lowering blood sugar in the treatment of a diabetic animal when administered orally in an effective blood sugar lowering amount, which comprises a hypoglycemic agent of the formula of claim 1 and a pharmaceutically acceptable carrier.

5. The composition of claim 4 wherein the hypoglycemic agent is present in an amount of from about 0.5 to about 90% by weight of the total composition.

6. The composition of claim 4 wherein the hypoglycemic agent is 1-cyclohexyl-3-{4-[2-(4-methyl-5-thiazolecarboxamido)ethyl]benzenesulfonyl}urea.

7. The composition of claim 4 wherein the hypoglycemic agent is 1-(bicyclo[2.2.1]hept-5-en-2-yl-endo-methyl)-3-{4-[2-(4-methyl-5-thiazolecarboxamido)ethyl]benzenesulfonyl}urea.

* * * * *